United States Patent
Bayliff et al.

(10) Patent No.: US 10,774,363 B2
(45) Date of Patent: Sep. 15, 2020

(54) METHODS OF PREDICTION OF WOUND HEALING

(71) Applicant: Woundchek Laboratories (US), Inc., Fall River, MA (US)

(72) Inventors: Simon W. Bayliff, North Yorkshire (GB); Patrick Brosnan, Quincy, MA (US)

(73) Assignee: WOUNDCHEK LABORATORIES (US), INC., Fall River, MA (US)

( * ) Notice: Subject to any disclaimer, the term of this patent is extended or adjusted under 35 U.S.C. 154(b) by 0 days.

(21) Appl. No.: 15/761,546

(22) PCT Filed: Sep. 26, 2016

(86) PCT No.: PCT/US2016/053674
§ 371 (c)(1),
(2) Date: Mar. 20, 2018

(87) PCT Pub. No.: WO2017/053931
PCT Pub. Date: Mar. 30, 2017

(65) Prior Publication Data
US 2018/0346959 A1 Dec. 6, 2018

Related U.S. Application Data

(60) Provisional application No. 62/233,088, filed on Sep. 25, 2015.

(51) Int. Cl.
| | | |
|---|---|---|
| *A01N 37/00* | (2006.01) | |
| *A61K 31/215* | (2006.01) | |
| *A01N 37/12* | (2006.01) | |
| *A01N 37/44* | (2006.01) | |
| *A61K 31/24* | (2006.01) | |
| *A01N 25/00* | (2006.01) | |
| *C12Q 1/37* | (2006.01) | |
| *C12Q 1/04* | (2006.01) | |

(52) U.S. Cl.
CPC .......... *C12Q 1/37* (2013.01); *C12Q 1/04* (2013.01); *G01N 2333/195* (2013.01); *G01N 2333/948* (2013.01); *G01N 2333/952* (2013.01); *G01N 2800/26* (2013.01)

(58) Field of Classification Search
None
See application file for complete search history.

(56) References Cited

U.S. PATENT DOCUMENTS

| | | |
|---|---|---|
| 2007/0275423 A1 | 11/2007 | Sebastian |
| 2009/0304778 A1 | 12/2009 | Sanders |

FOREIGN PATENT DOCUMENTS

| | | | |
|---|---|---|---|
| EP | 2896963 A1 | 7/2015 | |
| WO | 2005/042770 A2 | 5/2005 | |
| WO | WO-2005073721 A1 * | 8/2005 | ....... G01N 33/56955 |
| WO | 2006/030232 A2 | 3/2006 | |

OTHER PUBLICATIONS

Navia et al., "Structure of human neutrophil elastase in complex with a peptide chloromethyl ketone inhibitor at 1.84-A resolution," Proc. Natl., Acad. Sci. USA, 86:7-11 (1989).
Serena et al., "Protease Activity Levels Associated with Healing Status of Chronic Wounds", Conference poster, Wounds UK 2011 [retrieved on Nov. 22, 2016 from http://www.woundchek.com/uploads/downloads/posters_articles/Protease-Activity-Levels-Associated-with-Healing-Status-of-Chronic-Wounds.pdf].
ProteaseFluorescent Detection Kit, 2014 [retrieved Nov. 22, 2016 at http://sigmaaldrich.content/dam/sigma-aldrich/docs/Sigma/Bulletin/1/pf0100bul.pdf.
Woo et al., "A cross-sectional validation study of using NERDS and STONEES to assess bacterial burden", Ostomy Wound Management, 55(8):1-14 (2009).
International Search Report for corresponding PCT application No. PCT/US16/53674 dated Nov. 23, 2016.
International Search Report for corresponding European application No. 16849838.4, dated May 14, 2019.
Benson et al., "Bacterial protease activity, an indicator of bacteria pathogenicity in chronic wounds even in the absence of overt clinical signs—Clinical signs of infection and Bacterial Protease Activity (BPA)" (2013).

* cited by examiner

*Primary Examiner* — Layla Soroush
(74) *Attorney, Agent, or Firm* — DLA Piper LLP

(57) ABSTRACT

Methods of detecting a local infection, critical colonization, or infection in a wound, predicting wound healing in a wound, and detecting bacterial pathogenesis in a wound are provided.

12 Claims, 7 Drawing Sheets
Specification includes a Sequence Listing.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: N-methoxysuccinylalanine
<220> FEATURE:
<221> NAME/KEY: MOD_RES
<222> LOCATION: (4)..(4)
<223> OTHER INFORMATION: Valine chloromethyl ketone

<400> SEQUENCE: 1

Xaa Ala Pro Xaa
1
```

METHODS OF PREDICTION OF WOUND HEALING

PRIORITY

This application claims the benefit of U.S. Ser. No. 62/233,088, filed on Sep. 25, 2015, which is incorporated by reference herein in its entirety.

BACKGROUND OF THE INVENTION

Chronic wounds are open to the environment and are susceptible to contamination by bacteria, potentially leading to infection. Some of the consequences of a chronic wound infection are tissue breakdown, pain, additional impedance of the healing ability of the wound, amputation (e.g. in a diabetic foot ulcer) and systemic infection, which can be life-threatening. Identifying infection in chronic wounds is challenging because current clinical practice employs using clinical signs and symptoms ('NERDS') (Sibbald et al., Adv. Skin Wound Care 2006; 19(8): 447-61), which are not necessarily distinct from other conditions, such as chronic inflammation. Gardner et al., Ostomy Wound Manage. 2001; 47(1): 40-7. Bacteria and their proteases can stimulate a pro-inflammatory host response and, eventually, clinical signs due to this inflammatory response and tissue damage may be seen (FIG. 1). McCarty et al., Wound Repair and Regeneration 2012; 20: 125-36.

The host response often includes elevated inflammatory markers, e.g. cytokines including tumour necrosis factor alpha (TNFα) and interleukin-1 beta (IL-1β). Unfortunately, clinical signs may not be apparent if the inflammatory response is impaired or defective (e.g. when other co-morbidities are present, such as diabetes or immunosuppressive conditions), thereby increasing the risk of infection. Bacteria are in a pathogenic state when they are either in the process of, or they are capable of, causing disease, i.e. infection. One indication of pathogenicity is the production of enzymatic virulence factors or bacterial proteases. Bacterial pathogenesis is undesirable since, at this stage, the wound is in a part of the wound infection continuum that typically requires intervention (FIG. 6).

SUMMARY OF THE INVENTION

Embodiments of the invention provide methods of detecting local bacterial infection, critical bacterial colonization, or bacterial infection in a wound. The methods comprise contacting a test sample from a wound with a human neutrophil elastase inhibitor and a bacterial protease substrate; and detecting the amount of bacterial protease activity on the substrate. About 10 or more milliunits of equivalent bacterial protease activity can indicate a local bacterial infection, critical bacterial colonization, or bacterial infection in the wound. About 100 to 200 milliunits of equivalent bacterial protease activity can indicate that the wound is a non-healing wound. About 100 or more milliunits of equivalent bacterial protease activity can indicate a local bacterial infection, critical bacterial colonization, or bacterial infection in the wound. About 10 to 200 milliunits of equivalent bacterial protease activity can indicate that the wound is a non-healing wound. About less than 10 milliunits of equivalent bacterial protease activity can indicate no bacterial infection, bacterial contamination, or bacterial colonization. The wound can be a chronic wound. The bacterial protease substrate can be casein. The casein can be labeled with fluorescein iso-thiocyanate. The wound can have three or fewer, two or fewer, one, or zero NERDS clinical signs (i.e., non-healing wound, exudate, redness and bleeding, debris in the wound, and smell from the wound). The wound can have a bioburden of less than $10^5$ colony forming units/mL. The human neutrophil elastase inhibitor can be MeOSuc-Ala-Ala-Pro-Val-CMK)(SEQ ID NO:1), peptidyl chloromethyl ketones, turkey ovomucoid inhibitor, secretory leukocyte protease inhibitor domain 2, serpins α-1-proteinase inhibitor (α-1-PI), monocyte/neutrophil elastase inhibitor (MNEI), secretory leukocyte proteinase inhibitor (SLPI), elafin, soybean trypsin inhibitor, 3,4 dichloroisocoumarin, elastatinal, sivelestat, SSR 69071, sivelestat sodium tetrahydrate, and combinations thereof. The equivalent bacterial protease activity can be V8 equivalent bacterial protease activity. The method can further comprise administering treatment to the local bacterial infection, critical bacterial colonization, or bacterial infection in the wound.

Embodiments of the invention provide methods of predicting wound healing in a wound. The methods comprise contacting a test sample from the wound with a human neutrophil elastase inhibitor and a bacterial protease substrate and detecting the amount of bacterial protease activity on the bacterial protease substrate. About 10 or more or 100 or more milliunits of equivalent bacterial protease activity can indicate that the wound is a non-healing wound.

Embodiments of the invention provide methods of detecting bacterial pathogenesis in a wound. The methods comprise contacting a test sample from a wound with a human neutrophil elastase inhibitor and a bacterial protease substrate; and detecting the amount of bacterial protease activity on the substrate. About 10 or more or 100 or more milliunits of equivalent bacterial protease activity can indicate bacterial pathogenesis in the wound.

Embodiments of the invention provide methods of detecting a local bacterial infection, critical bacterial colonization, or bacterial infection in a wound. The method comprises obtaining a wound test sample, removing human neutrophil elastase from the sample, contacting the sample with a bacterial protease substrate, and detecting the amount of bacterial protease activity on the substrate. About 10 or more milliunits of equivalent bacterial protease activity can indicate a local bacterial infection, critical bacterial colonization, or bacterial infection in the wound. Treatment can be administered to the local bacterial infection, critical bacterial colonization, or bacterial infection in the wound. The human neutrophil elastase can be removed via sequestration or through contact with a cationic material.

There is a need for additional tools to help healthcare professionals assess chronic wounds. The compositions and methods of the invention can aid healthcare professionals through detection of bacterial protease activity for the assessment of bacterial pathogenesis.

BRIEF DESCRIPTION OF THE DRAWINGS

FIG. 6 panel (b) shows the stages in which bacterial pathogenesis and, hence, bacterial protease activity are involved ("?" means "may or may not be present").

DETAILED DESCRIPTION OF THE INVENTION

As used herein, the singular forms "a," "an," and "the" include plural referents unless the context clearly dictates otherwise. The term "about" in association with a numerical value means that the numerical value can vary plus or minus by 5% or less of the numerical value.

Chronic wounds include, but are not limited to, chronic cutaneous ulcers and non-healing burns, surgical, or trauma wounds. A chronic cutaneous ulcer is a wound that has failed to proceed through an orderly and timely series of events to produce a durable structural, functional, and cosmetic closure. The field of wound care also applies this definition to non-healing burns, surgical, or trauma wounds.

Chronic wounds are open to the environment and are susceptible to contamination by bacteria, potentially leading to infection. Some of the consequences of a chronic wound infection are tissue breakdown, pain, additional impedance of the healing ability of the wound, amputation (e.g. in a diabetic foot ulcer) and systemic infection, which can be life-threatening.

Figure 6:
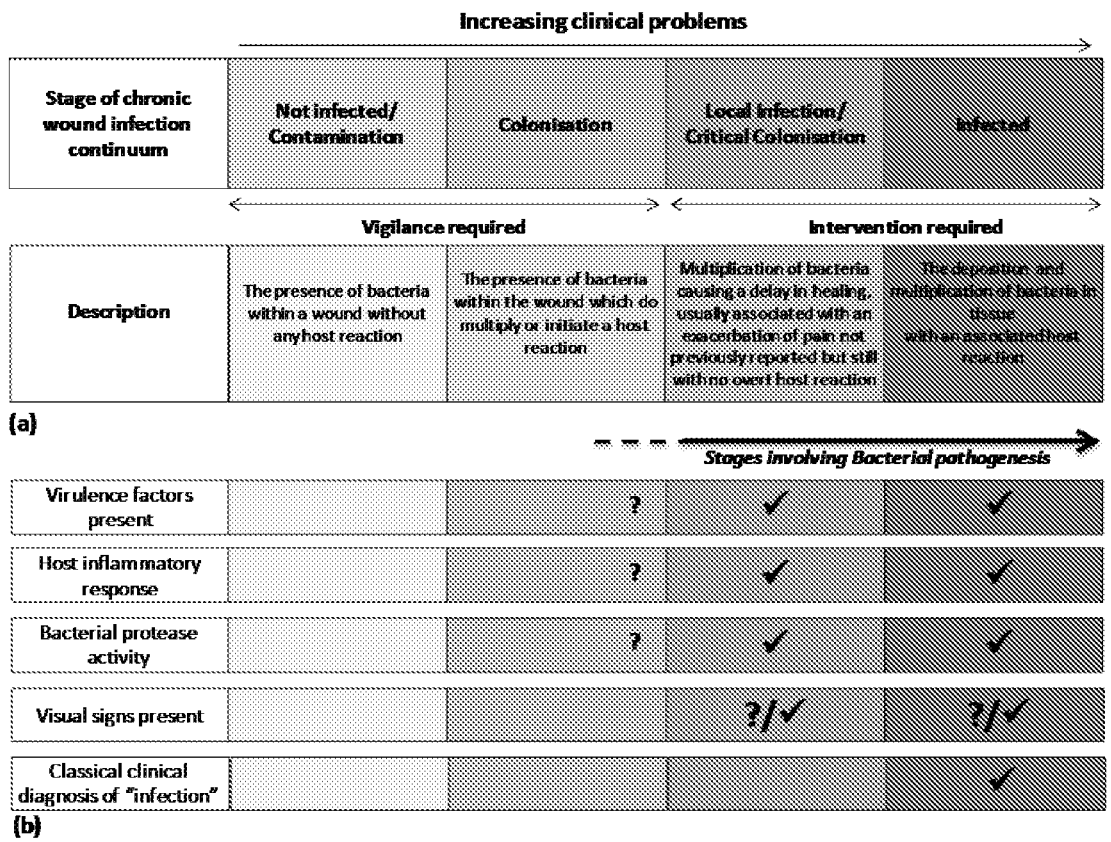
FIG. 6 panel (a) shows the wound infection continuum. Kingsley et al., Wounds UK 2004 Applied Wound Management supplement. The Wound Infection Continuum: a revised perspective. pp 13-18 (Ed: D Gray).

The use of the word "infection" in chronic wounds implies a binary condition—the wound is either "infected" or "not-infected"; yet this is an oversimplification of a series of pre-infection stages. The pre-infection and infection stages have been defined as a continuum of: bacterial contamination, bacterial colonization, critical bacterial colonization or local bacterial infection, and bacterial infection (Wound Infection in Clinical Practice: An international consensus. *International Wound Journal* 2008; 5 (3): 1-11), only some of which require intervention (FIG. 6A-B).

Critical bacterial colonization/local bacterial infection and bacterial infection are characterized by a host response i.e. clinical signs (FIG. 6A-B), whereas the prior stages are not associated with a host response.

Pre-infection stages (not infected/contamination, bacterial contamination) in the continuum are important because by recognition of pre-infected stages and appropriate intervention, the progression of a wound to infection can be avoided.

It is important to assess if a wound is merely contaminated with bacteria or colonized with bacteria versus critically bacterially colonized, locally bacterially infected, or bacterially infected, so appropriate patient management decisions can be made. Detection of bacterial protease activity in the early stages can aid healthcare professionals in this decision making process.

In terms of wounds:

"Not infected/bacterial contamination" means that there is presence of bacteria in a wound without any host reaction.

"Bacterial colonization" means that there is presence of bacteria in a wound, which are not multiplying or initiating a host reaction. Virulence factors, host inflammatory response, and bacterial protease activity may or may not be present.

"Local bacterial infection/critical bacterial colonization" means there is multiplication of bacteria in a wound causing a delay in healing. There is usually an exacerbation of pain not previously reported, but still no other host response. Virulence factors, host inflammatory response and bacterial protease activity are present. Visual signs of infection may or may not be present. Intervention (e.g., antibiotic treatment or debridement) is likely required.

"Bacterial infection" means the deposition and multiplication of bacteria in tissue of the wound with an associate host reaction. Virulence factors, host inflammatory response and bacterial protease activity are present. Visual signs of infection may or may not be present. The classic (e.g., NERDS) clinical diagnosis of infection is present. Intervention (e.g., antibiotic treatment or debridement) is likely required.

Once the body detects tissue damage and/or the presence of a foreign body such as bacteria, it elicits a host response, where white blood cells are immediately released to the wound site. These cells (e.g. neutrophils, monocytes) initiate the inflammatory response and the rapid release and activation of pro-inflammatory cytokines, including tumor necrosis factor-alpha (TNFα), which co-ordinates the resulting inflammatory response. Other inflammatory cytokines, such as interleukin-1 beta (IL-1β), are also produced as part of the normal host immune response to bacterial pathogenesis during the infection process. See id. Moreover, local elevated levels of such cytokines have been linked to critically colonized or infected wounds.

The primary role of the inflammatory process is to rid the wound of damaged tissue and foreign material such as bacteria, in addition to signalling the initiation of the next phases of healing. However, in chronic wounds, the normal pattern of events leading to healing is not followed, and persistent inflammation is observed. The presence of bacteria and their virulence factors, such as bacterial proteases, can exacerbate this problem and amplify an already hostile environment, eliciting a greater inflammatory response.

Figure 1:
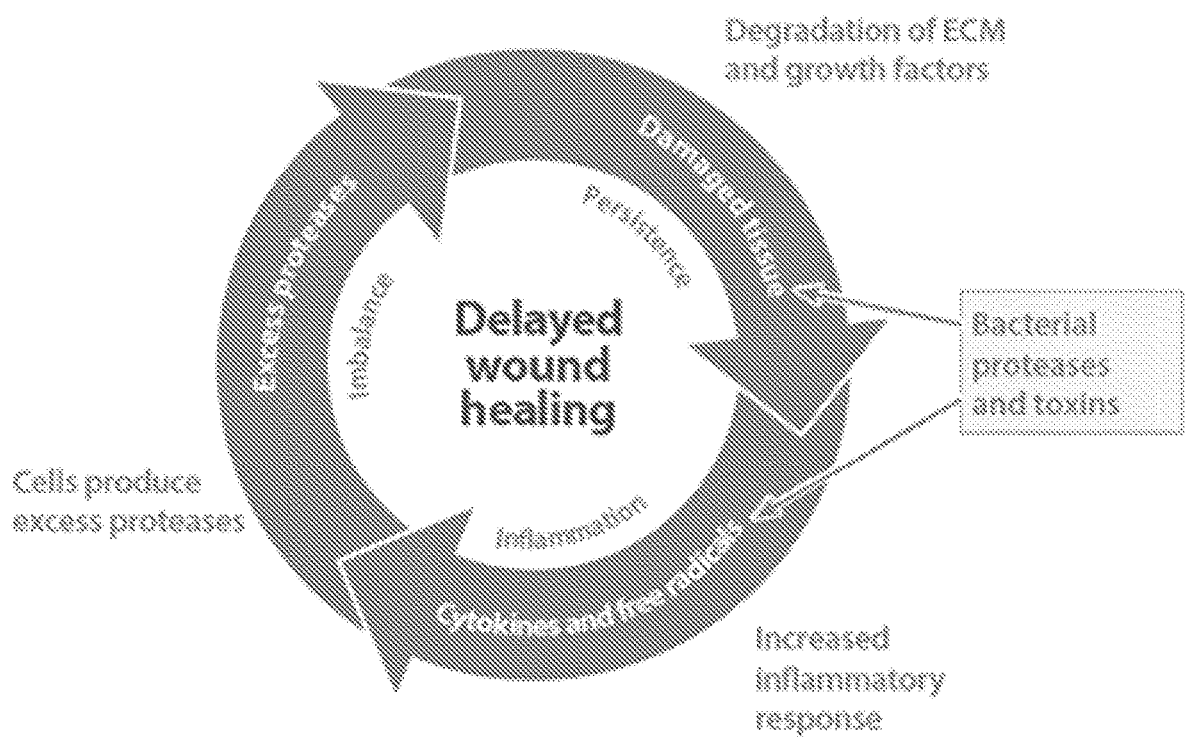
FIG. 1 shows the cycle of chronic wounds demonstrating involvement of bacterial proteases (ECM is extracellular matrix).

This process is depicted in FIG. 1. Therefore, pathogenic bacteria in the wound affect healing in many deleterious ways, including the effects of virulence factors such as bacterial proteases on the surrounding tissue, and the corresponding host inflammatory response that hinders healing from progressing, with resultant tissue damage.

Infection in chronic wounds is a process that starts with bacterial contamination of the wound and ultimately ends in obvious visual local and/or systemic infection, as a result of the host response to bacteria. There is a lack of specific, objective tests for diagnosing and/or assessing wound infection, and therefore healthcare professionals currently rely on visual cues, experience, and the presence of clinical signs. Assessment of chronic wounds for infection using sets of clinical signs have been reported and evaluated on many occasions. One of these sets uses an acronym: "NERDS" (Sibbald et al., *Adv. Skin Wound Care* 2006; 19(8): 447-61; Woo & Sibbald. *Ostomy Wound Manage.* 2009; 55(8): 40-48), which lists 5 clinical signs to be assessed (Table 1). The presence of 3 or more NERDS has been validated as being indicative of local bacterial infection/critical bacterial colonization.

TABLE 1

NERDS

| | |
|---|---|
| N | Non-healing |
| E | Exudate |
| R | Red & bleeding |
| D | Debris (in the wound) |
| S | Smell (from the wound) |

It is widely accepted that the use of clinical signs in assessing chronic wounds for infection can be challenging, especially when used by those without extensive experience, for the following reasons:
1. The infection process in wounds can be well established by the time visual clinical signs and symptoms are apparent, and thus the infection may be more difficult to treat once it has progressed to this stage. Ultimately, this can have serious consequences for the patient, such as amputation or systemic infection.
2. Visual signs may not always be present, especially in patients with co-morbidities such as diabetes and auto-immune diseases.
3. The clinical signs of infection and chronic inflammation in the absence of infection can overlap.

While diagnosis of wound infection is primarily based on clinical evaluation, it can be supported by microbiological data such as bioburden (CFU—amount of colony forming units per gram of tissue or mL of wound fluid) and/or species identification and antibiotic sensitivities. Typically, microorganisms isolated from chronic wounds are bacteria. Historically, a CFU threshold of "$10^5$ CFU or greater," per gram tissue or milliliter (mL) wound fluid, has been associated with wound infection. However, the various stages of chronic wound infection (FIG. 6) indicate that the mere presence of bacteria is not, by itself, an indicator of infection in chronic wounds. Infection may occur with bioburden levels below $10^5$ CFU per gram of tissue or mL of wound fluid; on the other hand, some wounds heal with bioburden levels above $10^5$ CFU per gram of tissue or mL of wound fluid. Healthcare professionals frequently culture wounds to confirm suspicion of infection and/or identify organism(s) present and their antibiotic sensitivities, only after a clinical diagnosis has been made.

Sample collection techniques from chronic wounds for microbiological evaluation vary. While some guidelines still advocate only the use of tissue biopsies when assessing bioburden in chronic wounds, other clinical guidelines state a tissue biopsy or a validated quantitative swab technique can be used. Biopsies are invasive and painful, can present additional risks for the patient and cannot always be justified as ethically appropriate when a quantitative swab is available. Quantitative cultures of wound surface swabs have been shown to be equivalent to tissue biopsies and are widely used in clinical practice.

Bacteria can be pathogenic and produce virulence factors, such as bacterial proteases, prior to infection and independently of inflammation. In some cases this may be before clinical signs and symptoms are apparent. Compositions and methods described herein provide methods of detection and identification of bacterial proteases in wounds. Therefore, the compositions and methods of the invention can help identify bacterial pathogenesis in chronic wounds which may fail, or be unable, to mount the visible host inflammatory response for the reasons noted above. For these reasons, the detection of bacterial protease activity, as an aid in the assessment of bacterial pathogenicity, is believed to be an important step forward in more accurately identifying non-healing or chronic wounds.

Bacterial proteases are produced by both Gram-negative and Gram-positive bacteria and can be extracellular or intracellular. While intracellular proteases are responsible for intracellular activities, such as sporulation and protein turnover and maturation, the primary role of extracellular proteases is to generate a nutrient source for the bacteria by hydrolyzing the peptide bonds within proteins. A negative consequence of this action is that, by degrading protein, the bacteria are able to cause harm to the host—either indirectly through degradation of host growth factors and their receptors, leading to an elevated and prolonged immune response, or directly by invading the underlying soft tissue.

A number of known proteases have been characterized from some of the frequently reported bacteria in chronic wounds (Table 2).

TABLE 2

Examples of proteases from relevant bacteria from chronic wounds and their functions.

| Bacterium | Protease | Protease Classification | Target |
|---|---|---|---|
| Staphylococcus aureus | SspA (V8) | Serine Protease | Antimicrobial peptides<br>Fibronectin-binding proteins (bacterial adhesion)<br>SspB (cysteine protease) activation<br>α1-antitrypsin |
| Pseudomonas aeruginosa | LasB | Metalloprotease | Antimicrobial peptides (LL-37)<br>Protease-activated receptor-2<br>Chemokines (RANTES, MCP-1, ENA-78)<br>Cytokines (IL-6, IL-8, IFN-γ)<br>Cytokine receptors (IL-6R)<br>Phagocyte functions (uPAR, fMLP receptor)<br>α1-antitrypsin |
| Proteus mirabilis | ZapA | Metalloprotease | Antimicrobial peptides (LL-37, hBD1)<br>Complement (C1q and C3)<br>Colonization |
| Enterococcus faecalis | GelE | Metalloprotease | Complement (C3)<br>Antimicrobial peptides (LL-37) |

The impact of bacterial proteases has been documented in a range of acute and chronic medical conditions, including cystic fibrosis, eye infections, and wound infections. While the skin provides a protective barrier against infection, once the epidermis has been breached, bacteria are able to colonize the underlying tissue, migrate from the initial site of entry, and invade the surrounding tissue. The presence of bacterial proteases, and additional disruption of the epithelial barrier by these enzymes, further compromises the protective barrier of the skin, leading to the colonization by other microbial species.

Figure 2:
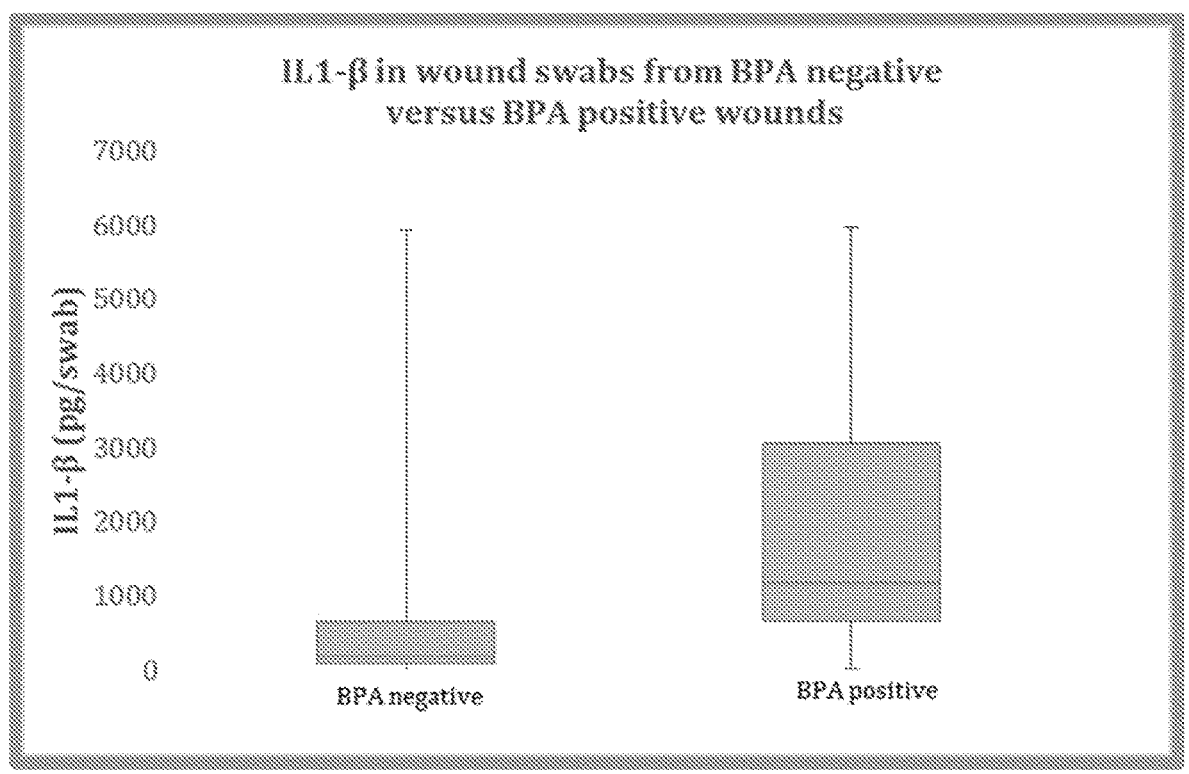
FIG. 2 shows significantly higher levels of IL1-β in "bacterial protease activity" (BPA) positive (2,065 pg/swab) versus BPA negative (722 pg/swab) wounds (p<0.0001).
Figure 3:
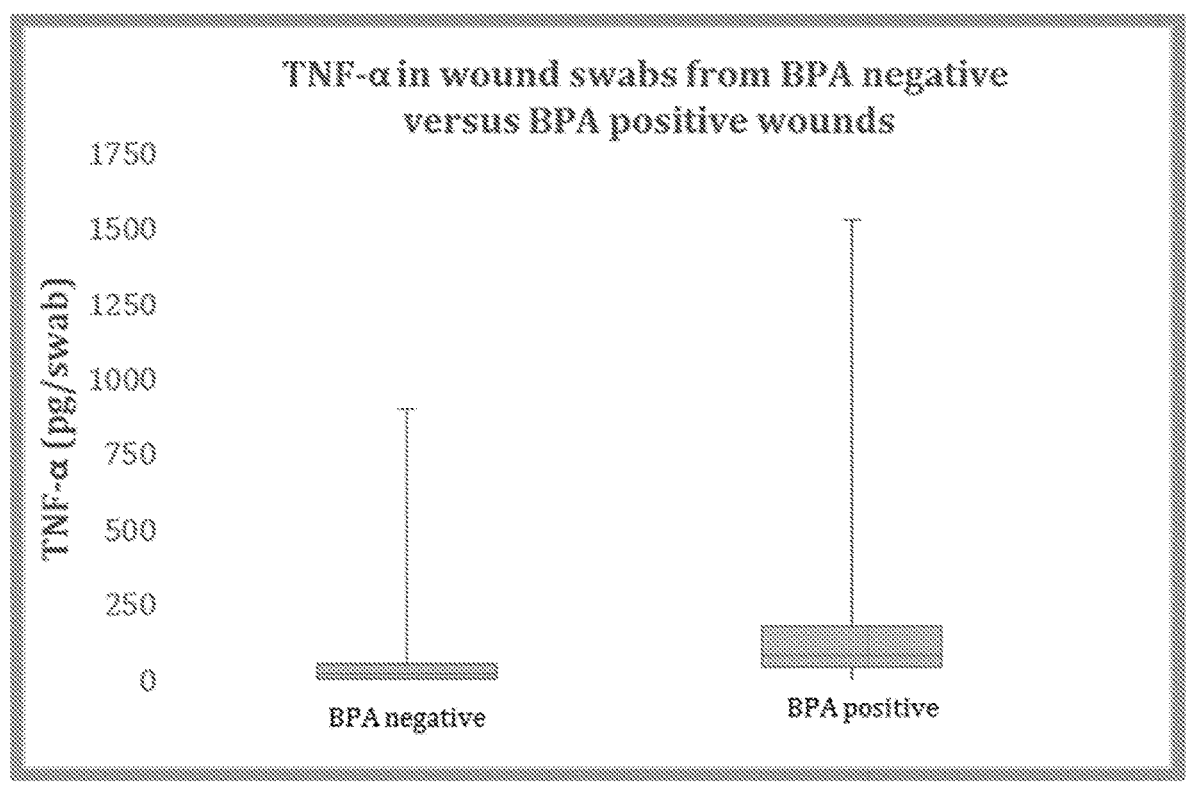
FIG. 3 shows significantly higher levels of TNF-α in BPA positive (167 pg/swab) versus BPA negative (56 pg/swab) wounds (p<0.0002).

Increased production of pro-inflammatory cytokines (e.g. IL1-β & TNF-α) is known to be one of the host responses to infection by pathogenic bacteria. The results in FIGS. 2 and 3 show that increased levels of IL1-β & TNF-α are detected when wounds test positive for BPA. However, the data shown in FIG. 5 reveals that increased BPA can be detected even when the wound is asymptomatic for infection (i.e., only 2 'NERDS' present). Therefore, the presence of bacterial proteases above a threshold level of activity can indicate to a clinician that the wound is progressing to the point when the host is mounting a biochemical response to the insult and the wound is developing towards infection (FIG. 6) that requires intervention (e.g., antibiotic treatment or debridement) even though overt signs are not obvious to the clinician.

Figure 4:
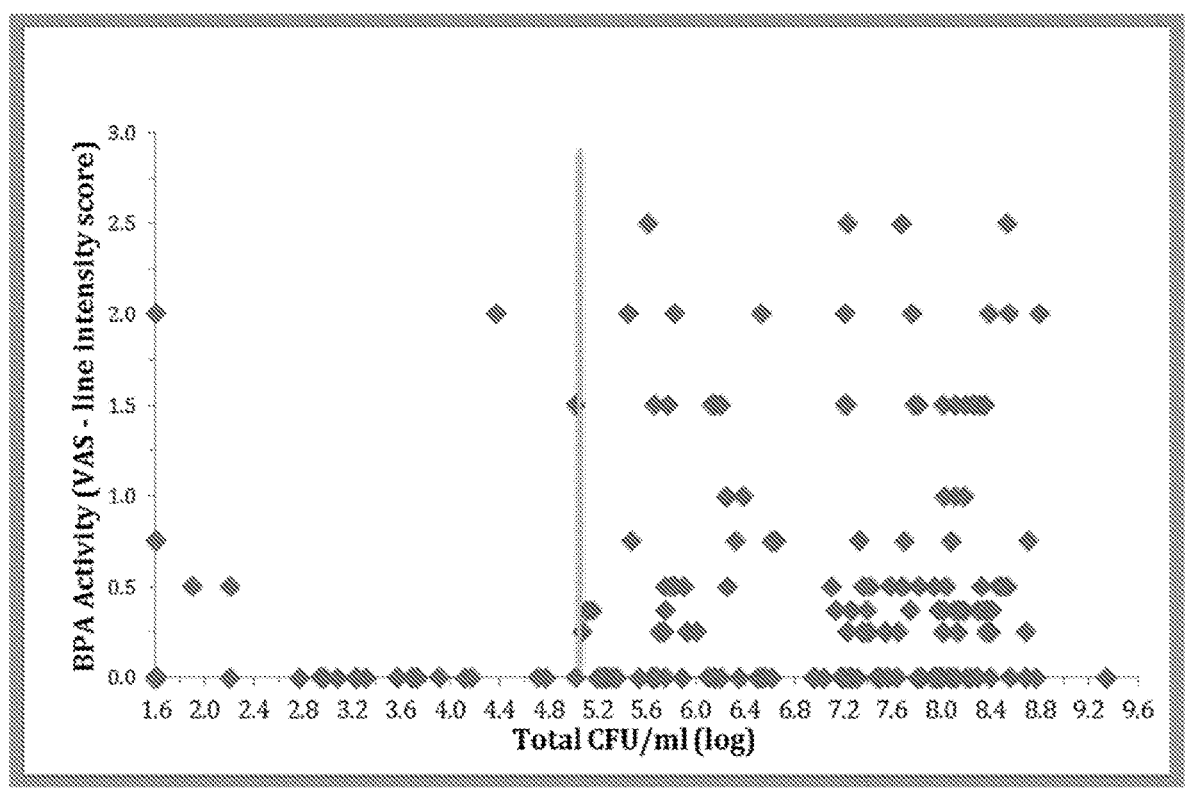
FIG. 4 shows BPA against bioburden (CFU/mL).

FIG. 4 demonstrates that BPA is detected much more frequently when the bioburden is >$10^5$ CFU/mL wound fluid. It is surprising that some wounds with a bioburden >$10^5$ CFU/mL wound fluid are BPA negative, whilst a few wounds with a bioburden <$10^5$ CFU/mL wound fluid are BPA positive. This observation is consistent with literature reports that wounds can heal when colonized with relatively high levels of bacteria whilst others succumb to infection when colonized by relative few of a highly virulent species of bacteria. As reported in the larger study of 366 wounds (see Example 2), a high proportion (72%) had bacterial counts >$10^5$ CFU/mL wound fluid but only 18% of this cohort of patients exhibited three or more clinical signs of infection. By contrast, around half of the wounds (49%) tested positive for BPA indicating that they are in a 'state of pathogenesis' i.e. the bacteria colonizing the wound are displaying pathogenic behaviour, with around three quarters of these patients being asymptomatic for infection.

Measurement of the activity of bacterial proteases can rely on their ability to degrade proteins. A bacterial protease will typically degrade or cleave a protein of choice (i.e. a substrate) at one or more sites. Protein substrates can be used to detect and quantify bacterial protease activity through, for example, conjugation with a fluorescent label.

Figure 7:
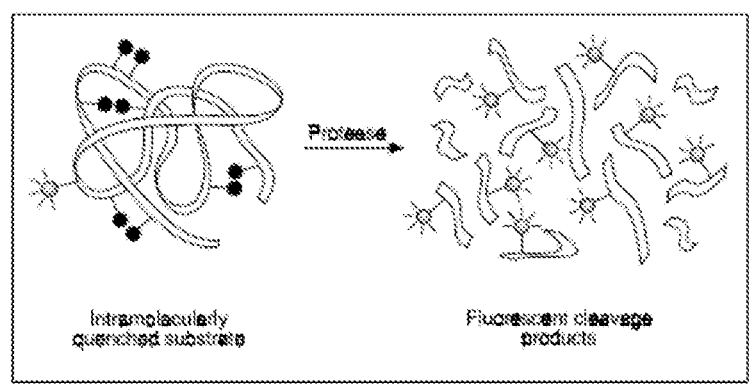
FIG. 7 shows emittance of fluorescence following substrate cleavage.

Any type of label or detection method for detection of bacterial protease activity can be used in the methods described herein. Bacterial protease substrates, for example, bacterial protease protein substrates, can be used in methods of the invention to detect bacterial protease activity. Bacterial protease substrates can be labeled with, for example, fluorescent labels such as fluorescein isothiocyanate (FITC), which are highly fluorescent, react with amino groups of most proteins, and require only a simple reaction to yield a FITC-labelled protein. The fluorescent properties of these labelled substrates changes upon digestion by the bacterial protease, resulting in a measurable indication of proteolysis. The fluorescence in the intact protein substrate is suppressed due to self-quenching of the conjugated label; subsequent cleavage of the substrate into peptides by bacterial protease activity reduces the extent of self-quenching, resulting in the emittance of detectable fluorescence (FIG. 7). The rate of change in fluorescence is therefore directly related to the level of bacterial protease activity in a particular sample.

A bacterial protease substrate can also be labeled with, for example, organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Cleavage of bacterial protease substrates can also be detected without the use of labels, using for example, surface plasmon resonance biosensors.

Bacterial proteases can be measured by a variety of techniques that utilize bacterial protease substrates, for example, casein, bacterial adhesions, SspB, α1-antitrypsin, LL-37, protease-activated receptor-2, RANTES, MCP-1, ENA-78, IL-6, IL-8, IFN-γ, IL-6R, uPAR, fMLP receptor, hBD1, antimicrobial peptides, and Complement Clq and C3.

A bacterial protease substrate, such as casein, can be used in the methods of the invention. Casein is a broad spectrum substrate with specificity against all four proteolytic classes of bacterial proteases (i.e., serine, aspartic, cysteine and metalloproteases), thus allowing for the detection of a wide range of bacterial proteases.

Methods of detection of cleavage of casein include, for example, labeling casein with FITC as described above or coupling casein with activated resorufin [N-(resorufin-4-carbonyl)piperidine-4-carbonic acid N-hydroxysuccinimide ester]. This substrate can be measured both spectrophotometrically and fluorimetrically. By treatment with proteases, resorufin-labeled peptides are released from casein. The concentration of these resorufin-labeled peptides in the supernatant is equivalent to the proteolytic activity present. Furthermore, cleavage of casein can be detected with the use Folin's reagent. When casein is digested tyrosine is liberated along with other amino acids and peptide fragments. Folin and Ciocalteus Phenol (Folin's reagent) reacts with free tyrosine to produce a blue chromophore that is quantifiable and can be measured as an absorbance value with a spectrophotometer.

The host response to pathogenic bacteria is inflammation. Therefore, the main contribution of host proteases will be neutrophil derived, the two main classes of which are serine proteases and matrix metalloproteinases (MMPs). The predominant neutrophilic serine protease in chronic wounds is human neutrophil elastase (HNE), which will degrade casein. The predominant neutrophilic MMPs in chronic wound fluid are MMP-8, a collagenase, and MMP-9 and MMP-2, which are both gelatinases.

Inhibitors of serine proteases and matrix metalloproteinases can be used in methods described herein to reduce cleavage of bacterial protease substrates by host factors.

The main substrate preferences of MMP-8, 9, and 2, as their names suggest, are collagen and gelatin, rather than casein (Table 3), because their core biological role during inflammation is degradation of the extracellular matrix. Additionally, MMP-9 and 2, both gelatinolytic enzymes, require specific amino acid sequences on both sides of the cleavage site. Using these amino acid recognition sequences, proteins containing these sequences have been identified from protein databases. A limited list of putative physiologic substrates was identified and casein was not identified as a protein containing any of these recognition sequences. Kridel et al. *J. Biol. Chem.* 2001; 276(23): 20572-8.

Inhibitors of MMP-2, MMP-8, and MMP-9 can be used in methods disclosed herein. Examples include MMP-2 Inhibitor I, MMP-2 Inhibitor II, MMP-2 Inhibitor III, MMP-2 Inhibitor IV, MMP-2 Inhibitor V, actinonin, Chlorhexidine, Pyridoxatin, MMP-8 Inhibitor I, doxycycline, antibody AB0041, antibody AB0046, TIMP-1.

TABLE 3

Substrate preferences of MMP-8-9 and 2 (from Whittaker & Ayscough, Celltransmissions, 17: 3-14 (2001)).

| MMP | Alternative name | Substrates |
| --- | --- | --- |
| MMP-2 | Gelatinase A 72 KDa | Collagens (I, IV, V, VII, X, XI and XIV); gelatin; elastin; fibronectin; aggrecan; Myelin basic protein; osteonectin; laminin-1; MMP-1; MMP-9; MMP-13 |
| MMP-8 | Neutrophil collagenase | Collagens (I, II, III, V, VII, VIII and X); gelatin; aggrecan; fibronectin |
| MMP-9 | Gelatinase B | Collagens (IV, V, VII, X and XIV); gelatin; entactin; aggrecan; elastin; fibronectin; osteonectin; plasminogen; Myelin basic protein; IL-1β |

As HNE can degrade casein, it can be inhibited in detection methods by using an inhibitor of cleavage of the substrate prior to use (that is, prior to exposure to wound fluid). A specific inhibitor of HNE is, for example, chloromethyl ketone (CMK) peptide inhibitor (MeOSuc-Ala-Ala-Pro-Val-CMK)(SEQ ID NO:1). This inhibitor is irreversible, and the peptide sequence is preferred and selective for HNE, therefore specifically removing its activity from the wound fluid sample. Other HNE inhibitors include, for example, peptidyl chloromethyl ketones, turkey ovomucoid inhibitor, secretory leukocyte protease inhibitor domain 2, serpins α-1-proteinase inhibitor (α-1-PI), monocyte/neutrophil elastase inhibitor (MNEI, also called Serpin B1), and the chelonianin family of canonical inhibitors that includes secretory leukocyte proteinase inhibitor (SLPI), elafin, soybean trypsin inhibitor, 3,4 dichloroisocoumarin, elastatinal, sivelestat, SSR 69071, sivelestat sodium tetrahydrate and combinations thereof.

HNE can also be removed from a test sample via other methods including, for example, contacting the sample with cationic material. Interfering HNE activity can be removed from samples by pretreatment with cation exchange resin (such as sepharose (such as SP sepharose), phosphocellulose (such as phosphocellulose P11), Sephadex resins, and combinations thereof)). The cationic material can be present in beads, membranes, non-woven fibers and/or cotton swabs, sponges, filters, wipes, pads, and dressings.

HNE can also be sequestered by contacting the sample with fibers (e.g., cotton fibers), beads, filters, pads, sponges or the like. The fibers, beads, filters, pads, sponges, or the like can have peptide-cellulose conjugates incorporated therein, The fibers, beads, filters, pads, sponges and the like can be dialdehyde, carboxymethylated, sulfonated, and phosphorylated fibers, beads, filters, pads, or sponges. Polycarboxylic acid crosslinked fibers, beads, filters, pads, sponges and the like can also be used. In an example, the sample collection device, for example, a swab, comprises fibers as described above.

Assay Procedures

Assay procedures can be performed in any assay format, such as a microtiter plate format for the measurement of bacterial protease activity in wound fluid samples, utilizing, for example, a FITC-casein substrate. Other assay formats include, for example, immunoassays, lateral flow immunoassays, colorimetric immunoassays, radiometric immunoassays, fluorometric immunoassays, chemiluminescent immunoassays, test tubes, microplate wells, and combinations thereof.

A test sample can be a sample of fluid or tissue from a wound. Wound fluid is any wound exudate or other fluid that is present at the surface of a wound, or that is removed from a wound surface by aspiration, absorption or washing. Methods can be carried out on wound fluid or tissue that has been removed from the body of the patient, but can also be performed on wound fluid or tissue in situ. Wound fluid or tissue can be mammalian wound fluid or tissue such as human wound fluid or tissue.

A bacterial protease isolated from *Staphylococcus aureus* (e.g., Endoproteinase Glu-C or V8 bacterial protease) (e.g., a commercially available bacterial protease) can be used to create a standard curve for an assay. A standard curve can be used to determine the concentration of bacterial proteases in a sample. A standard curve is obtained by relating a measured quantity to the concentration of the protease of interest in "known" samples, i.e., standards of known concentration. These standards provide a reference to determine unknown concentrations of bacterial proteases in a wound sample. The amounts of standards should span the whole range of concentrations expected to be found in the "unknown" sample concentration.

The V8 bacterial protease can be used as a representative sample of a bacterial protease. A standard curve can be created by, for example, preparing a 3, 5, 6, 7, 8, 9, or 10 level serial dilution series of a protease such as V8.

Wound fluid samples can be extracted by eluting a collection swab in an elution buffer. The bacterial protease (e.g. V8) curve standards and wound fluid samples are added to the microtiter plate in duplicate wells. The elution buffer is also run in duplicate to serve as a blank.

An inhibitor of human proteases, e.g., an HNE inhibitor, for example, Me-O-Suc-Ala-Ala-Pro-Val-CMK (SEQ ID NO:1) can be added to samples in sufficient quantity to ensure that any bacterial protease substrate (e.g., casein) digestion is not a result of human protease (e.g., HNE) activity in the sample. The bacterial protease substrate/human protease inhibitor (e.g. FITC-casein substrate/HNE inhibitor) working solution, prepared in a buffer, can be added to the wound fluid samples and curve standards (e.g., V8 curve standard) on the microplate. Immediately after the addition of the substrate working solution, the plate is read by a fluorescent microplate reader at intervals (e.g., 1, 2, 3, 4, 5, or more minute intervals) to obtain the kinetic curve over a total time span of 5, 10, 20, 30, 45, 60 or more minutes.

The raw data output from the fluorescent microplate reader is expressed in relative fluorescence units (RFUs). The RFUs generated by the standards and samples are plotted against time, and a linear regression analysis is performed to calculate the slope of the response (RFU/minute) for each well. The slopes of the replicates of each standard level are averaged and plotted against their concentrations. Linear regression analysis of this standard curve is performed to generate a linear equation that describes the relationship between RFU/minute and bacterial protease concentration. This equation can then be used to interpolate the concentration of the unknown samples from the slope of their kinetic curves. The resulting concentrations of bacterial protease in the replicates of each wound fluid sample on the plate are averaged.

Where V8 bacterial protease is used in the Examples to produce the standard curve in the assay, the results are reported as V8 equivalent bacterial protease activity. The results, however, can be calculated with any type of bacterial protease to yield "equivalent bacterial protease activity." The final bacterial protease activity level can be extrapolated to the liquid volume used for the swab elution step and is reported in mU (milliunits of proteases).

Any bacterial protease can be used to produce a standard curve in an assay. The standard curve can be produced in advance of testing wound samples or can be produced at the same time the wound samples are tested.

In embodiments, a tested wound is considered a non-healing wound (or a "local bacterial infection/critical bacterial colonization" wound or a "bacterial infected" wound) by detecting an amount of bacterial proteases in a wound test sample, using for example, an iCasein assay, at or above a defined threshold. The defined threshold can be about 10, 25, 50, 75, 100, 110, 120, 125, 126, 130, 136, 140, 146, 150, 160, 170, 175, 180, 190, 200 or more mU (milliunits) of equivalent bacterial protease activity (for example 10 or more, 25 or more, 50 or more, 75 or more, 100 or more, 125 or more, 150 or more, 175 or more, or 200 or more mU of V8 bacterial protease equivalent activity or other bacterial protease equivalent activity).

In another embodiment a tested wound is considered a non-healing wound (or a "local bacterial infection/critical bacterial colonization" wound or a "bacterial infected" wound) by detecting an amount of bacterial proteases in a wound test sample, in for example, an iCasein assay, within a defined range. The defined range can be about 100 to about 200, about 100 to about 150, about 126 to about 146, about 100 to about 175, about 125 to about 175, about 130 to 140, about 10 to about 200, about 50 to 200, about 75 to 200, or about 150 to about 200 mU of V8 bacterial protease equivalent activity or other bacterial protease equivalent activity. About less than 10 milliunits of equivalent bacterial protease activity can indicate no bacterial infection, bacterial contamination, or bacterial colonization.

Non-healing wounds (or a "bacterial local infection/critical bacterial colonization" wound or a "bacterial infected" wounds) identified by the methods of the invention can be treated with, for example antibiotics (e.g., topical or systematic), debridement (e.g., sharp, enzyme, mechanical, biological or autolytic debridement), surgical closure by skin graft, skin equivalent, pedicled or free flap), wound cleansing, hyperbaric oxygen therapy, autograft, allograft, or extracellular matrix replacement.

In an embodiment, a tested wound is considered a healing wound (or a "not infected/bacterial contamination" wound or a "colonization" wound) by detecting an amount of bacterial proteases in a wound test sample, using for example, an iCasein assay, below a defined threshold. The defined threshold can be about 10, 25, 50, 75, 100 or less mU (milliunits) of equivalent bacterial protease activity (for example 10 or less, 25 or less, 50 or less, 75 or less, 100 or less mU of V8 bacterial protease equivalent activity or other bacterial protease equivalent activity).

In another embodiment a tested wound is considered a healing wound (or a "not infected/bacterial contamination" wound or a "colonization" wound) by detecting an amount of bacterial proteases in a wound test sample, in for example, an iCasein assay, within a defined range. The defined range can be about 10 to 100, about 50 to about 100, about 10 to about 50, about 10 to about 75 mU of V8 bacterial protease equivalent activity or other bacterial protease equivalent activity.

In one embodiment, a healing wound (or a "not infected/bacterial contamination" wound or a "colonization" wound) identified by the methods of the invention can be monitored via the methods of the invention for progression along the wound continuum.

It is noted that purified V8 bacterial protease spiked onto wound sampling swabs can elicit a positive at around 10 mU or about 10% of the clinically derived threshold. The clinical threshold, while expressed as 'V8 equivalent bacterial protease activity' is not a purified protease like V8 bacterial protease, but a mixture of enzymes in a complex matrix.

The "yardstick" used to establish the cut-off level for assays of the invention (e.g., the iCasein assay) is clinical assessment of chronic wounds using the NERDs set of clinical signs. The presence of 3 or more NERDS is classified as positive for critical bacterial colonization/bacterial pathogenesis. Preliminary data has indicated that the prevalence of 3 or more NERDS is approximately 15%, and thus the sample size required for a test of power at 80%, and at a significance level of 0.05, in this clinical testing is n=342.

A range of chronic wound types have been sampled, including but not limited to, leg ulcers, diabetic foot ulcers, pressure ulcers, and non-healing burns and surgical wounds. The clinical signs & symptoms (i.e. NERDS) are recorded prior to collecting the swabs. The assays (e.g., the iCasein assay) can be performed on the samples collected.

Prior to the instant invention it was believed that bacteria secreted virulence factors when turning to a pathogenic state from a non-pathogenic state by switching on certain genes. That is, a binary condition such that the detection or non-detection of the secreted virulence factors would be sufficient. However, the link between bacterial proteases and wound non-healing occurs above a defined threshold of the amount of bacterial proteases in a wound test sample. That is, a non-healing wound (or a local bacterial infection, critical bacterial colonization, or bacterial infection) can be identified by detecting an amount of bacterial proteases over a defined threshold. Statistical analysis was used to determine the defined threshold of bacterial protease activity, measured using the iCasein assay (see Example 2), which samples have 3 or more NERDS. When iCasein assay values are above the final established cut-off, the samples were classified as bacterial protease activity positive. When the iCasein values are equal to or below the established cut-off, the samples were classified as bacterial protease activity negative. Bacterial protease positive samples indicate non-healing wounds (and local bacterial infection, critical bacterial colonization, and bacterial infection), while bacterial protease negative samples indicate healing wounds (or not infected/contaminated or colonized).

One embodiment of the invention provides a method of detecting a local bacterial infection, critical bacterial colonization, or bacterial infection in a wound. The method comprises contacting a test sample from a wound with a human neutrophil elastase inhibitor and a bacterial protease substrate and detecting the amount of bacterial protease activity on the bacterial protease substrate. Ten or more milliunits of V8 equivalent bacterial protease activity or other equivalent bacterial protease activity indicates a local bacterial infection, critical bacterial colonization, or bacterial infection in the wound. About 100 to 200 milliunits of V8 equivalent bacterial protease activity (or other equivalent bacterial protease activity) can indicate that the wound is a non-healing wound. About 100 or more milliunits of V8 equivalent bacterial protease activity (or other equivalent bacterial protease activity) indicates a local bacterial infection, critical bacterial colonization, or bacterial infection in the wound. About 10 to 200 milliunits of V8 equivalent bacterial protease activity (or other equivalent bacterial protease activity) can indicate that the wound is a non-healing wound. The wound can be a chronic wound. The substrate can be casein. The substrate can be labeled with fluorescein iso-thiocyanate or other suitable label. The wound can have three or fewer, two or fewer, one, or zero NERDS clinical signs (i.e., non-healing wound, exudate, redness and bleeding, debris in the wound, and smell from the wound). It is surprising and unexpected that the methods of the invention can detect non-healing wounds, local infection/critical colonization wounds and infected wounds in the absence of 1 or more, or 2 or more, or 3 or more NERDS factors. The wound can have a bioburden of less than about $10^5$ colony forming units per gram of tissue or mL of wound fluid. It is surprising and unexpected that the methods of the invention can detect non-healing wounds, local infection/critical colonization wounds and infected wounds in the absence of a bioburden of greater than $10^5$ CFU per gram of tissue or mL of wound fluid.

It is surprising and unexpected that the methods of the invention can detect healing wounds, "not infected/bacterial contamination" wounds, and "colonization" wounds in the presence of 3 or more NERDS factors. It is surprising and unexpected that the methods of the invention can detect healing wounds, "not infected/bacterial contamination" wounds, and "colonization" wounds in the presence of a bioburden of greater than $10^5$ CFU per gram of tissue or mL of wound fluid.

An embodiment of the invention provides a method predicting wound healing in a wound. The method comprises contacting a test sample from the wound with a human neutrophil elastase inhibitor and a bacterial protease substrate and detecting the amount of bacterial protease activity on the bacterial protease substrate. About 10 or more or about 100 or more milliunits of V8 equivalent bacterial protease activity (or other equivalent bacterial protease activity) indicates that the wound is a non-healing wound. About less than 10 milliunits of equivalent bacterial protease activity can indicate no bacterial infection, bacterial contamination, or bacterial colonization.

An embodiment of the invention provides a method of detecting bacterial pathogenesis (the presence of bacteria causing infection) in a wound. A test sample from a wound is contacted with a human neutrophil elastase inhibitor and a bacterial protease substrate. The amount of bacterial protease activity on the substrate is detected. About ten or more or about 100 or more milliunits of V8 equivalent bacterial protease activity (or other equivalent bacterial protease activity) indicates bacterial pathogenesis in the wound.

Any of the above methods for detection of local infection, critical colonization, or infection in a wound, detection of bacterial pathogenesis, or detection of non-healing wounds may alternatively use a defined threshold or amount of V8 equivalent bacterial protease activity of about 10, 25, 50, 75, 100, 110, 120, 125, 126, 130, 136, 140, 146, 150, 160, 170, 175, 180, 190, 200 or more mU (milliunits) (for example 10 or more, 25 or more, 50 or more, 75 or more, 100 or more, 125 or more, 150 or more, 175 or more, or 200 or more mU of V8 bacterial protease equivalent activity or other bacterial protease equivalent activity).

Any of the above methods for detection of local infection, critical colonization, or infection in a wound, detection of bacterial pathogenesis, or detection of non-healing wounds may alternatively use a defined range of about 100 to about 200, about 100 to about 150, about 126 to about 146, about 100 to about 175, about 125 to about 175, about 130 to 140, about 10 to about 200, about 50 to 200, about 75 to 200, or about 150 to about 200 mU of V8 bacterial protease equivalent activity or other bacterial protease equivalent activity.

An embodiment of the invention provides a method of detecting a local infection, critical colonization, or infection in a wound. The method comprises contacting a test sample from a wound with a human neutrophil elastase inhibitor (e.g., Me-O-Suc-Ala-Ala-Pro-Val-CMK) (SEQ ID NO:1) and a casein substrate, which can be labeled with fluorescein iso-thiocyanate. The amount of bacterial protease activity on the substrate is determined wherein about 10 or more milliunits of V8 equivalent bacterial protease activity or other bacterial protease equivalent activity indicates a local infection, critical colonization, or infection in the wound.

An embodiment of the invention provides a method of detecting a local bacterial infection, critical bacterial colonization, or bacterial infection in a wound. The method comprises contacting a test sample from a wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the bacterial protease substrate is determined wherein about 100 or more milliunits of V8 equivalent bacterial protease activity (or other bacterial protease equivalent activity) indicates a local infection, critical colonization, or infection in the wound.

An embodiment of the invention provides a method of detecting a local bacterial infection, critical bacterial colonization, or bacterial infection in a wound. The method comprises contacting a test sample from a wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the substrate is determined wherein about 10 to 200 milliunits of V8 equivalent bacterial protease activity (or other bacterial protease equivalent activity) indicates that the wound is a non-healing wound.

An embodiment of the invention provides a method of predicting wound healing in a wound. The method can comprises contacting a test sample from the wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the substrate is determined. About 10 or more milliunits of V8 equivalent bacterial protease activity (or other bacterial protease equivalent activity) indicates that the wound is a non-healing wound.

An embodiment of the invention provides a method of predicting wound healing in a wound. The method can comprises contacting a test sample from the wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the substrate is determined. About 100 or more milliunits of V8 equivalent bacterial protease activity (or other bacterial protease equivalent activity) indicates that the wound is a non-healing wound.

An embodiment of the invention provides a method of detecting bacterial pathogenesis in a wound. The method comprises contacting a test sample from a wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the substrate can be determined. About 10 or more milliunits of V8 equivalent bacterial protease activity (or other bacterial protease equivalent activity) indicates bacterial pathogenesis in the wound.

An embodiment of the invention provides a method of detecting bacterial pathogenesis in a wound. The method comprises contacting a test sample from a wound with a human neutrophil elastase inhibitor (e.g., Me-O-Suc-Ala-Ala-Pro-Val-CMK)(SEQ ID NO:1) and a casein substrate, which can be labeled with fluorescein iso-thiocyanate. The amount of bacterial protease activity on the substrate can be determined. About 100 or more milliunits of V8 equivalent bacterial protease activity (or other bacterial protease equivalent activity) indicates bacterial pathogenesis in the wound.

An embodiment of the invention provides methods of detecting a local bacterial infection, critical bacterial colonization, or bacterial infection in a wound. The method comprises obtaining a wound test sample, removing human neutrophil elastase from the sample, contacting the sample with a bacterial protease substrate, and detecting the amount of bacterial protease activity on the substrate. About 10 or more milliunits of equivalent bacterial protease activity can indicate a local bacterial infection, critical bacterial colonization, or bacterial infection in the wound. Treatment can be administered to the local bacterial infection, critical bacterial colonization, or bacterial infection in the wound. The human neutrophil elastase can be removed via sequestration or through contact with a cationic material.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Duplicate swabs were taken from 186 chronic wounds (including leg ulcers (LU), diabetic foot ulcers (DFU), and pressure ulcers (PU) & other non-healing wounds) and comingled to ensure homogeneity. One swab was extracted for testing in a laboratory bacterial protease assay using casein as substrate, including an inhibitor of human neutrophil elastase ('iCasein' assay), and for analysis for cytokines IL-13 and TNF-α, and for culture for quantitative microbiology. The second swab was tested on a prototype rapid lateral flow point of care bacterial protease lateral flowtest. The BPA is expressed as line intensity on the lateral flow test line evaluated using a visual analogue scale (VAS). Appearance of any test line (i.e. ≥0.25 VAS) on the bacterial protease lateral flow test is indicative of presence of BPA ("BPA positive").

The results are summarised in FIGS. 2, 3, and 4. The mean levels of pro-inflammatory cytokines IL1-β (FIG. 2) and TNF-α (FIG. 3) are significantly higher in wounds that are BPA positive versus wounds that are BPA negative. There is a marked increase in the number of wounds yielding positive results on a rapid point of care bacterial protease lateral flow test when the total bioburden exceeds $10^5$ CFU/mL (FIG. 4).

Example 2

Wound fluid swabs were taken from 366 chronic wounds (including LU, DFU, PU & other non-healing wounds) and were extracted into an elution buffer for testing in the iCasein assay and assessment by the clinician for the number of clinical signs of infection ('NERDS') present. Wounds were classified as BPA positive if an iCasein activity threshold (125 milliunits/swab) was exceeded. An additional swab was taken for culture and quantitative microbiology.

A standard curve was created by preparing a 5 level serial dilution series of V8. The V8 curve standards and wound fluid samples were added to the microtiter plate in duplicate wells. The elution buffer was also run in duplicate to serve as a blank. An HNE inhibitor Me-O-Suc-Ala-Ala-Pro-Val-CMK (SEQ ID NO:1) was added in sufficient quantity to ensure that any casein digestion is not a result of HNE activity in the sample. A sufficient quantity can be, for example, 20 µl of 1 mM stock in a total volume of 220 µl, i.e., 91 µM. The FITC-casein substrate/HNE inhibitor working solution, prepared in a buffer, was added to the wound fluid samples and V8 curve standards on the microplate. Immediately after the addition of the substrate working solution, the plate was read by a fluorescent microplate reader at one minute intervals to obtain the kinetic curve over a total time span of 30 minutes.

Figure 5:
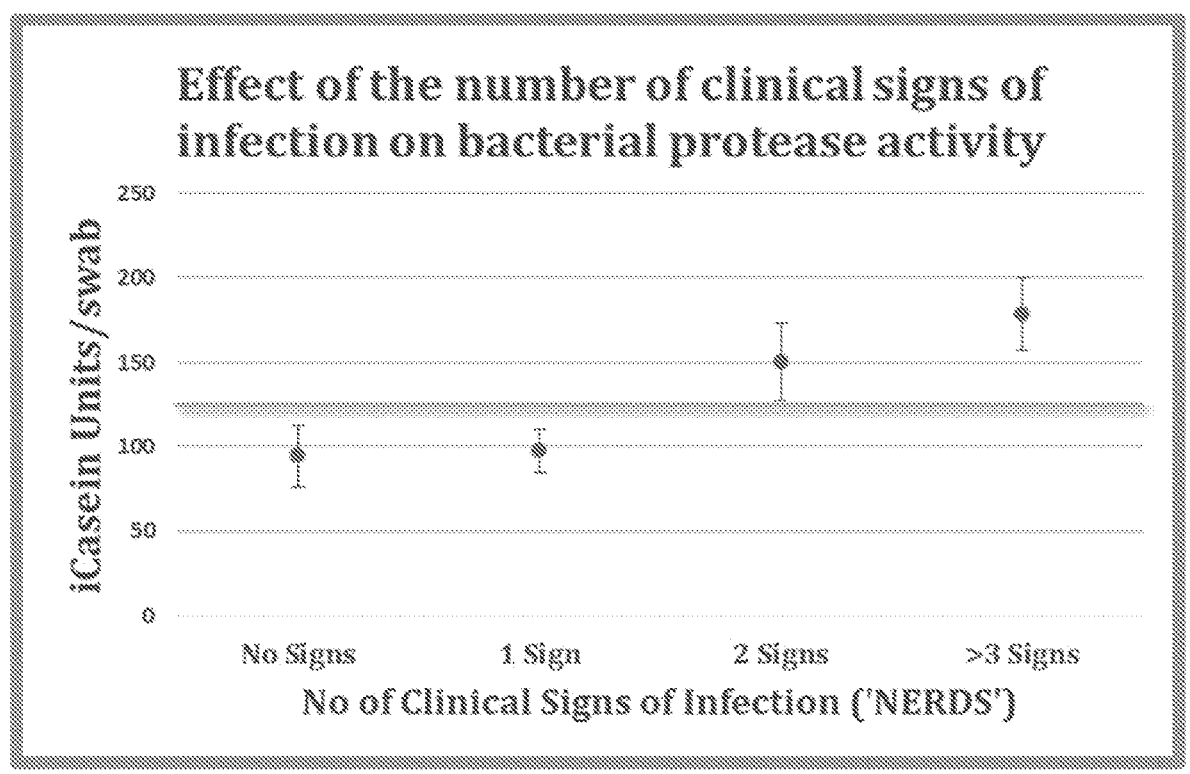
FIG. 5 shows median bacterial protease activity in wounds exhibiting differing numbers of clinical signs of infection. Note that the Y-axis is actually iCasein V8 bacterial protease equivalent milliunits/swab (and not iCasein Units/swab).

This example evaluated the relationship between the BPA, clinical signs of infection ('NERDS') and bioburden levels in wounds. FIG. 5 demonstrates the median BPA in wound fluid increases when two signs or more signs are present.

A high proportion of wounds (72%) had bacterial counts $>10^5$ per mL but only a relatively small proportion (18%) exhibited 3 or more clinical signs of infection. In contrast, nearly half of the wounds (49%) tested positive for BPA.

Example 3: The Establishment of an ICV8 Bacterial Protease (Equivalent) Threshold Value This example discusses and provides a threshold (Cut Off) Value for an iCasein V8 ("ICV8") bacterial protease reference standard result when compared with the clinical assessment of the infected status of a chronic wound.

In a cross sectional multi-centered study, the chronic wounds of 493 patients were clinically assessed for infection status using the standard subjective NERDS approach. A sample of fluid from these wounds was concurrently taken and prepared for the later laboratory based measurement of bacterial protease iCasein V8 ("ICV8").

The presence of a specific amount of bacterial protease is an indicator of wound infection and can be determined by the reference ICV8 method.

Clinician based assessments of chronic wounds for the designation of a wound as infected or not is a subjective protocol based on a count of key factors (NERDS) indicative of wound infection. (<3 factors=not infected 23 factors=infected)

ICV8 values were transformed for use in ANOVA and Multivariate analysis. Clinical determined infected status was applied as a binary.

| a. Infected status | 1 = infected | 0 = not infected |
|---|---|---|
| b. ICV8 Cutoff | 1 = above | 0 = below. |

Significance Levels and Confidence intervals of 95% were applied throughout.

There is a significant difference between the means & medians of ICV8 levels (i.e. direct or transformed) in the two groups of wounds clinically classified as infected or non-infected. ROC analysis provides an unweighted threshold at approximately ICV8=151 mU and a suggested model is an ICV8 Threshold—136 mU in order to optimize Sensitivity alongside other diagnostic indicators.

CONCLUSION

There is a statistically significant difference in ICV8 levels obtained from clinically assessed infected and non-infected chronic wounds. There is a good positive correlation between the value of measured ICV8 and the prevalence of classified infected wounds. There is an acceptable discrimination between Infected and non-infected wounds and a threshold value of ICV of about 136 mU, obtained by ROC analysis and by Multivariate canonical discrimination, can be suggested to optimize sensitivity and hence minimize false negative counts.

Example 4

Wound fluid swabs taken from 145 chronic wounds (including venous, arterial and mixed aetiology leg ulcers, pressure ulcers and diabetic foot ulcers) in United States wound clinics were tested for the presence of bacterial protease activity using a prototype point of care lateral flow swab test. Following the test, the wounds were monitored for 12 weeks. Of the total of 145 wounds, 89 (59.7%) were non-healing after 12 weeks and just under half (66, 45.5%) were positive for bacterial protease activity at week 0. For wounds yielding positive tests for bacterial protease activity, 48 out of 66 were non-healing after 12 weeks (Positive Predictive Value for Non-Healing=72.7%, 95% Confidence Intervals 61-82%). Significantly more of the wounds that tested negative for bacterial protease activity healed by 12 weeks (48% vs 27%, p=0.011).

---

---

We claim:

1. A method of detecting a local bacterial infection, critical bacterial colonization, or bacterial infection in a wound comprising:
   (a) contacting a test sample from a wound with a mixture of N-(Methoxysuccinyl)-Ala-Ala-Pro-Val-chloromethyl ketone (a human neutrophil elastase inhibitor) and casein (a bacterial protease substrate); and
   (b) detecting the amount of bacterial protease activity on the substrate;
   wherein about 10 or more milliunits of equivalent bacterial protease activity indicates a local bacterial infection, critical bacterial colonization, or bacterial infection in the wound.

2. The method of claim 1, wherein about 100 to 200 milliunits of equivalent bacterial protease activity indicates that the wound is a non-healing wound.

3. The method of claim 1, wherein about 100 or more milliunits of equivalent bacterial protease activity indicates a local bacterial infection, critical bacterial colonization, or bacterial infection in the wound.

4. The method of claim 1, wherein about 10 to 200 milliunits of equivalent bacterial protease activity indicates that the wound is a non-healing wound.

5. The method of claim 1, wherein the wound is a chronic wound.

6. The method of claim 1, wherein the wound has, two or fewer, one, or zero NERDS clinical signs: non-healing wound, exudate, redness and bleeding, debris in the wound, and smell from the wound.

7. The method of claim 1, wherein the wound has a bioburden of less than $10^5$ colony forming units per mL or gram of test sample.

8. The method of claim 1, further comprising administering treatment to the local bacterial infection, critical bacterial colonization, or bacterial infection in the wound.

9. A method of detecting bacterial pathogenesis in a wound comprising:
   (a) contacting a test sample from a wound with N-(Methoxysuccinyl)-Ala-Ala-Pro-Val-chloromethyl ketone (a human neutrophil elastase inhibitor) and casein (a bacterial protease substrate); and
   (b) detecting the amount of bacterial protease activity on the substrate;

wherein about 10 or more or 100 or more milliunits of equivalent bacterial protease activity indicates bacterial pathogenesis in the wound.

10. A method of detecting a local bacterial infection, critical bacterial colonization, or bacterial infection in a wound comprising:
   (a) obtaining a wound test sample;
   (b) removing N-(Methoxysuccinyl)-Ala-Ala-Pro-Val-chloromethyl ketone (a human neutrophil elastase inhibitor) from the sample;
   (c) contacting the sample with a and casein (a bacterial protease substrate); and
   (d) detecting the amount of bacterial protease activity on the substrate;

wherein about 10 or more milliunits of equivalent bacterial protease activity indicates a local bacterial infection, critical bacterial colonization, or bacterial infection in the wound.

11. The method of claim 10, further comprising administering treatment to the local bacterial infection, critical bacterial colonization, or bacterial infection in the wound.

12. The method of claim 10, wherein the human neutrophil elastase is removed via sequestration or through contact with a cationic material.

* * * * *